United States Patent
Jensen et al.

(10) Patent No.: US 6,500,004 B2
(45) Date of Patent: Dec. 31, 2002

(54) ENDODONTIC SEALING COMPOSITIONS AND METHODS FOR USING SUCH COMPOSITIONS

(75) Inventors: Steven D. Jensen, South Jordan, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/736,729

(22) Filed: Dec. 14, 2000

(65) Prior Publication Data

US 2002/0123024 A1 Sep. 5, 2002

(51) Int. Cl.⁷ .................................................. A61C 5/00
(52) U.S. Cl. ...................... 433/228.1; 433/224; 523/116
(58) Field of Search .......................... 433/81, 224, 226, 433/228.1; 523/116

(56) References Cited

U.S. PATENT DOCUMENTS

| | | |
|---|---|---|
| 3,715,331 A | 2/1973 | Molnar ........................ 260/41 |
| 3,882,600 A | 5/1975 | Plymale |
| 3,925,895 A | 12/1975 | Kliment et al. ................. 32/15 |
| 3,959,212 A | 5/1976 | Rockett et al. .......... 260/42.53 |
| 3,997,504 A | 12/1976 | Plymale |
| 4,259,117 A * | 3/1981 | Yamauchi et al. ............. 106/35 |
| 4,499,251 A | 2/1985 | Omura et al. |
| 4,515,930 A | 5/1985 | Omura et al. |
| 4,525,493 A | 6/1985 | Omura et al. |
| 4,539,382 A | 9/1985 | Omura et al. |
| 4,612,384 A | 9/1986 | Omura et al. |
| 4,657,941 A | 4/1987 | Blackwell et al. |
| 4,669,983 A | 6/1987 | Bunker |
| 4,670,576 A | 6/1987 | Bunker |
| 4,806,381 A | 2/1989 | Englebrecht et al. |
| 4,813,876 A | 3/1989 | Wang |
| 4,816,495 A | 3/1989 | Blackwell et al. |
| 4,872,936 A | 10/1989 | Engelbrecht |
| 4,886,843 A | 12/1989 | Walton ........................ 522/174 |
| 4,966,934 A | 10/1990 | Huang et al. |
| 5,055,497 A | 10/1991 | Okada et al. |
| 5,089,051 A | 2/1992 | Eppinger et al. |
| 5,192,815 A | 3/1993 | Okada et al. |
| 5,306,338 A | 4/1994 | Tsunekawa |
| 5,326,263 A | 7/1994 | Weissman ................... 433/224 |
| 5,338,773 A | 8/1994 | Lu et al. |
| 5,367,002 A | 11/1994 | Huang et al. |
| 5,540,766 A | 7/1996 | Castellani .................... 106/35 |
| 5,859,089 A * | 1/1999 | Qian .......................... 523/116 |
| 6,133,339 A * | 10/2000 | Xie et al. ................... 523/116 |
| 6,353,041 B1 | 3/2002 | Qian |

FOREIGN PATENT DOCUMENTS

| | | |
|---|---|---|
| JP | 60-45510 | 3/1985 |
| JP | 61-151104 | 7/1986 |
| JP | 70-82115 | 3/1995 |
| JP | 80-99811 | 4/1996 |
| JP | 90-25208 | 1/1997 |

* cited by examiner

*Primary Examiner*—Nicholas D. Lucchesi
*Assistant Examiner*—Melba Bumgarner
(74) *Attorney, Agent, or Firm*—Workman, Nydegger & Seeley

(57) ABSTRACT

Endodontic sealant compositions and methods for sealing a root canal using sealant or other filling materials. The compositions include one or more resins that promote adhesion to hydrophilic dental tissues. Examples include alkyl methacrylates and derivatives thereof, such as alkylamino methacrylates and oxyphosphoro methacrylates. The compositions include a radio opacifying agent, so that they may be seen using X-rays, and one or more polymerization initiators to effect curing, typically both chemical and photo initiators to yield a dual cure sealant composition. The compositions are introduced into the root canal using a narrow cannula coupled to a high pressure hydraulic delivery device. Additional pressure may be applied to the sealant compositions using a syringe-like plunger introduced within a cylindrical access hole drilled through the crown of the tooth. A curing lamp may be used to cure the top layer of the sealant composition to provide a rigid bonding surface to which a composite resin can chemically bond or adhere.

29 Claims, 6 Drawing Sheets

ENDODONTIC SEALING COMPOSITIONS AND METHODS FOR USING SUCH COMPOSITIONS

BACKGROUND OF THE INVENTION

1. The Field of the Invention

The invention is in the field of compositions and methods for sealing a root canal during an endodontic procedure. More particularly, the invention involves compositions having enhanced adhesion to hydrophilic dental tissues found within root canals which assists their ability to effectively seal and protect a newly cleaned root canal. Such compositions are preferably radiopaque and are cured more rapidly compared to existing endodontic sealing compositions, thus allowing for quicker placement of a final filling or crown to complete the root canal procedure.

2. The Relevant Technology

Following an endodontic root canal procedure, in which the root canal is cleaned using special root canal tools and irrigation devices, it is important to fill and seal the evacuated root canal in order to preserve the dead tooth from further decay that might compromise the integrity of the tooth and cause infection. In a typical procedure, one or more soft, resilient, needle-like inserts known as "gutta percha" points are inserted in each root canal branch in order at least partially seal and fill the root canal.

The term "gutta percha" refers to a rubbery material derived from natural rubber, typically blended with zinc oxide. This particular rubbery material is preferred because it is compressible, flexible and relatively soft so that it can be used to fill voids within the exposed root canal. The gutta percha points are typically impregnated with other materials such as radiopaque solids, zinc oxide, for its medicinal properties, and other passive or active ingredients as desired. It is impossible, however, to completely seal a root canal from all ingress of fluids, which may be laden with bacteria, using gutta percha alone. Conventional techniques require multiple gutta percha cones per canal and laborious "later condensation" techniques. For some, it requires a heating the gutta percha in an attempt to make it flow into the lateral canals. However, this technique, coupled with the properties of gutta percha, make it hard to achieve fine adaptation to canal walls and flow into the dentinal tubules.

The filling and sealing of the root canal can be further enhanced by inserting flowable materials, such as antiseptic pastes and/or sealing resins along with the gutta percha points. Due to the high viscosity of typical antiseptic pastes, such as zinc oxide/eugenol, or sealing resins, which tend to be epoxy-based, such materials are first applied to the gutta percha and then inserted into the root canal along with each gutta percha point. Alternatively, they may be inserted using a lentalo applicator. In this manner, it is hoped that the remaining spaces between the gutta percha points and the root canal can be filled with the antiseptic paste or resin. In addition, it is hoped that the epoxy-based resin will help to seal the root canal.

One of the drawbacks of using conventional pastes or resins is that such materials tend to be hydrophobic. This renders such materials somewhat incompatible with dental tissues within the root canal, which are highly mineralized, somewhat moist and therefore extremely hydrophilic. The hydrophilic nature of the root canal environment inhibits wetting and adhesion of the root canal by hydrophobic materials. As a result, conventional antiseptic pastes and epoxy-based resins actually form a poor seal between the gutta percha points and the walls of the root canal, thus potentially providing access for microbes and infection.

A further problem of conventional antiseptic pastes and epoxy-based endodontic sealing resins are their inability to adequately penetrate into, wet and seal the lateral canals which extend laterally from the root canal into the root of the tooth. Occasionally, the inability to seal the lateral fissures using conventional pastes and/or epoxy-based resins creates one more place where microbes may establish a beach head and be capable of festering over time.

In addition to the inability of the antiseptic pastes or epoxy-based resins to adequately adhere to and seal the root canals and lateral fissures, another problem relates to the inability to evacuate all air bubbles or pockets from the root canal during placement of the gutta percha points and associated pastes or resins. As the gutta percha point coated with pastes or resins is packed into the root canal, or as sealers are worked in with a lentalo applicator, upper portions of the gutta percha or sealer can seal against the root canal wall, thus trapping air between the coronal portion and the root canal apex. Failure to remove such air pockets creates an area where subsequent infection can fester. Although gutta percha is highly radiopaque, even if the dentist can observe whether or not the root canal spaces have been adequately filled, the task of removing the packed materials and repeating the procedure is time consuming, expensive, and uncomfortable for the patient. Moreover, many sealer pastes are only moderately radiopaque and include silver powder, which makes the root canal too dark.

Lateral condensation using gutta percha is typically not sufficient to force the highly viscous pastes, gutta percha, or resins into the lateral canals. Merely pushing against the top portion of the gutta percha does not exert very much force on the flowable pastes or resins, since pressurized fluids can escape around the space between the gutta percha, lateral condensation instrument, and the root canal rather than being forced into the lateral canals or other areas occupied by air bubbles or pockets.

Finally, in the case where nonpolymerizable pastes, such as zinc oxide/eugenol are used, the chemistries of such materials can interfere with the ability of subsequently placed prosthetic filling materials to chemically bond or adhere to the tooth.

In short, it would be an improvement of the art of endodontic procedures to provide compositions and methods which improved the ability of an endodontic sealing material to penetrate, wet, adhere and seal to the dental tissues surrounding or defining the root canals.

It would be an additional improvement in the art to provide compositions and methods that provided for a more thorough evacuation of air bubbles or air pockets within the root canal, as well as including lateral spaces or canals connected to or in communication with the main root canal branches.

It would also be an improvement in the art to provide compositions and methods which yielded a filled root canal in which the sealing material did not interfere with the ability of a subsequently placed composite resin material to bond or adhere to the tooth.

It would be a further advancement in the art if such compositions and methods provided for the ability to allow for variable curing times such as faster or slower curing, to account for variations in difficulty and success that may be experienced by a dental practitioner.

It would yet be an improvement in the art if such compositions could also be light cured so as to reduce the time a patient must wait until the root canal sealing material was sufficiently cured to permit subsequent filling of the remainder of the tooth with a composite filling material.

Such compositions and methods for more effectively filling and sealing a root canal and providing a bonding surface are disclosed and claimed herein.

SUMMARY AND OBJECTS OF THE INVENTION

The present invention encompasses adhesive resins for use in filling and/or sealing a root canal during an endodontic procedure, as well as procedures that employ such compositions. The adhesive sealing and filling resins according to the present invention include a component that is compatible with a hydrophilic environment and that allows the resin to wet, penetrate and adhere to the dental tissue surrounding the root-canal. In addition, such resins are better able to penetrate into and seal the lateral canals that often extend from the main root canal branches. In order to assist such sealing, improved methods for applying a pressure to the sealing and filling resins are also disclosed.

The adhesive sealing and filling compositions of the present invention include one or more polymerizable methacrylate monomers, preferably including an oxyphosphorus constituent for better adhesion, a radio opacifying agent, and one or more types of polymerization initiators. The composition may also include other additives such as diluent or complementary monomers, fillers, antimicrobial agents, plasticizers, solvents and the like.

An example of an adhesive methacrylate resin within the scope of the invention is bis-glycidyl dimethacrylate phosphate. An example of a radio opacifying agent according to the present invention is bismuth chloride. An example of a suitable diluent monomer is urethane dimethacrylate. Examples of polymerization initiators include chemical initiators, such as peroxides and amines, and photoinitiators, such as camphor quinone. Because it is typically impossible to completely cure a polymerizable resin using photo initiation as the sole means to initiate polymerization, particularly all the way down to the apex of the root canal, it will typically be advantageous to include a chemical initiator so as to ensure complete curing of the polymerizable monomer over time.

In a preferred embodiment, the chemical initiator will be selected and included in an amount so as to provide sufficient time for a dental practitioner to properly place the composition within the root canal and ensure good penetration into the lateral canals. In most cases, it will be advantageous to include a chemical curing agent that causes the polymerizable resin to cure within a time period of from about 15 minutes to about 2 hours, more preferably from about 30 minutes to about one hour.

In the event that the dentist determines that the endodontic sealing resin has been properly placed, the dentist can then rapidly cure the upper portion of the resin by means of the inclusion of a photoinitiator and the application of curing radiation, such as light generated by a conventional dental curing lamp. In this way, the dentist can cure the top few millimeters of endodontic sealing resin by means of the curing lamp so as to provide a hardened upper surface to which a composite filling material can be chemically bonded or adhered. This greatly speeds up the time in which a dentist can complete the endodontic procedure.

In the case of resins or sealers that are only chemically cured, the dentist must ensure adequate curing and solidification prior to placing a composite resin on top of the sealing resin. In some cases, the patient must sit in the dental chair for half an hour, to an hour or more, wasting both the dentist's and the patient's time. In many cases, the dentist will simply place a temporary filling material over the uncured resin and send the patient home with the result being the patient must return for a follow-up visit in which the dentist removes the temporary filling material and replaces it with the final restorative material.

Embodiments that include "dual cure" compositions (i.e., compositions that are capable of both chemical and light cure) provide a tremendous advantage over single cure resins. Although such dual cure capability has been available for luting cements, it has never been available for root canal sealing or filling materials. The chemical cure properties provide the aforementioned window of time to account for variations in procedure difficulty and success, while the light cure properties provide for almost immediate curing of the top layer by photoinitiated curing once it has been determined that the sealing or filling material has been properly placed. This provides a tremendous advantage for both the dentist and the patient because it obviates the need for a patient to either sit in the dental chair wasting time while the resin cures or else having to make a return visit to receive the final filling material. Another advantage is that the resins chemically cure in a relatively short period of time compared to conventional sealers, thus minimizing the tendency of monomers to leach into the surrounding tissue.

In another aspect of the invention, the adhesive resins are placed within the root canal by means of a narrow cannula or syringe tip device attached to a high pressure hydraulic device or system. Due to the viscosity of the mixed polymerizable resins or non resinous pastes such as zinc oxide pastes, coupled with the small size of typical root canals, it is difficult to express sealing resins or pastes through cannulas or syringe tips capable of entering into a root canal. For this reason, the inventive methods according to the present invention contemplate the use of high pressure syringes or other hydraulic devices, such as those disclosed in copending U.S. application Ser. No. 09/467,419, filed Dec. 20, 1999, and presently assigned to Ultradent Products, Inc. For purposes of disclosure, the foregoing U.S. patent application is incorporated herein by specific reference.

In a preferred method for placing adhesive resins within a root canal, the apex of the root canal is first sealed using a gutta percha cone. In order to ensure that the apex has been adequately sealed, a "tug back" seal is formed. That is, the gutta percha cone is first inserted and then removed. If it can be removed with little or no force, the gutta percha point is trimmed to yield a larger diameter tip and reinserted into the apex. This process is repeated until there is "tug back," thus indicating that the fit between the gutta percha point and the apex is sufficiently tight to adequately seal the apex and prevent flow of sealing or filling material therethrough into the surrounding bone tissue.

After sealing the apex, the sealing or filling resin is inserted into the root canal using a narrow cannula tip. The cannula tip is placed within the root canal near the apex and slowly raised as the root canal is filled with resin, thus minimizing or eliminating the formation of air pockets or bubbles as the sealing or filling resin is progressively placed within the root canal. This procedure greatly improves the ability of the resin to initially purge most or all of the air from within the root canal compared to simply dipping a gutta percha point in the resin and stuffing the point into the root canal, or spinning the material with lentalo applicators, as is typically done using conventional methods.

In order to further ensure that the endodontic sealing resin penetrates and seals every space, irregularity, or lateral canal of the root canal, it may be advantageous to apply pressure to the resin after it has been initially placed within the root canal. This may be accomplished, for example, by inserting a plunger of complimentary size into the hole previously bored through the crown of the tooth. The plunger will typically include a plunger rod and a resilient plunger plug, such as a plug made of gutta percha material. In a preferred method for forming a plunger, excess gutta percha material trimmed from a gutta percha cone used to fill a root canal is wrapped around the end of a stiff metallic wire or plunger rod. The wire and gutta percha are then placed through the hole of the tooth. The wire is heated, which momentarily causes the gutta percha to melt and coalesce together, thus forming a resilient plunger plug having a size complementary to the hole in the tooth.

Inward pressure of the plunger from the crown toward the apex of the root canal exerts pressure on the resinous sealing material, thus forcing the material into the cracks, crevices and lateral canals of the root canal. Because the resilient gutta percha plug seals against the walls defining the hole through the crown of the tooth, the resinous material is not able to squeeze out between the tooth and the gutta percha plug but is instead forced into the aforementioned spaces, crevices or canals. In this manner, the resinous sealing or filling material is able to substantially form a hermetic seal of the root canal.

Providing a more complete seal of the root canal greatly increases the ability of the sealed root canal to resist the ingress of fluids into the root canal. Such fluids, if allowed to enter a root canal, may introduce microbes capable of infecting the tooth and surrounding bone. In improving the ability of the resinous sealing material to actually seal the root canal, including lateral canals and other crevices typically hard to fill, the inventive compositions and methods provide a tremendous advantage over conventional compositions and methods in yielding a tooth that is more resistant to microbial leakage.

In view of the foregoing, it is an object of the invention to provide compositions and methods which improve the ability of an endodontic sealing material to wet, adhere and seal to the dental tissue surrounding or defining the root canals.

It is an additional object of the invention to provide compositions and methods that provide for a more thorough evacuation of air bubbles or air pockets within the root canal, as well as lateral spaces or canals connected to, or in communication with, the main root canal branches.

It is also an object of the invention to provide compositions and methods which yield a filled root canal having a material to which a subsequent composite resin material can chemically bond or adhere.

It is a further object of the invention to provide compositions and methods which provide for variable curing times, such as faster or slower curing, to account for variations in difficulty and success that may be experienced by a dental practitioner.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE PREFERRED EMBODIMENTS

I. Introduction

Figure 1:
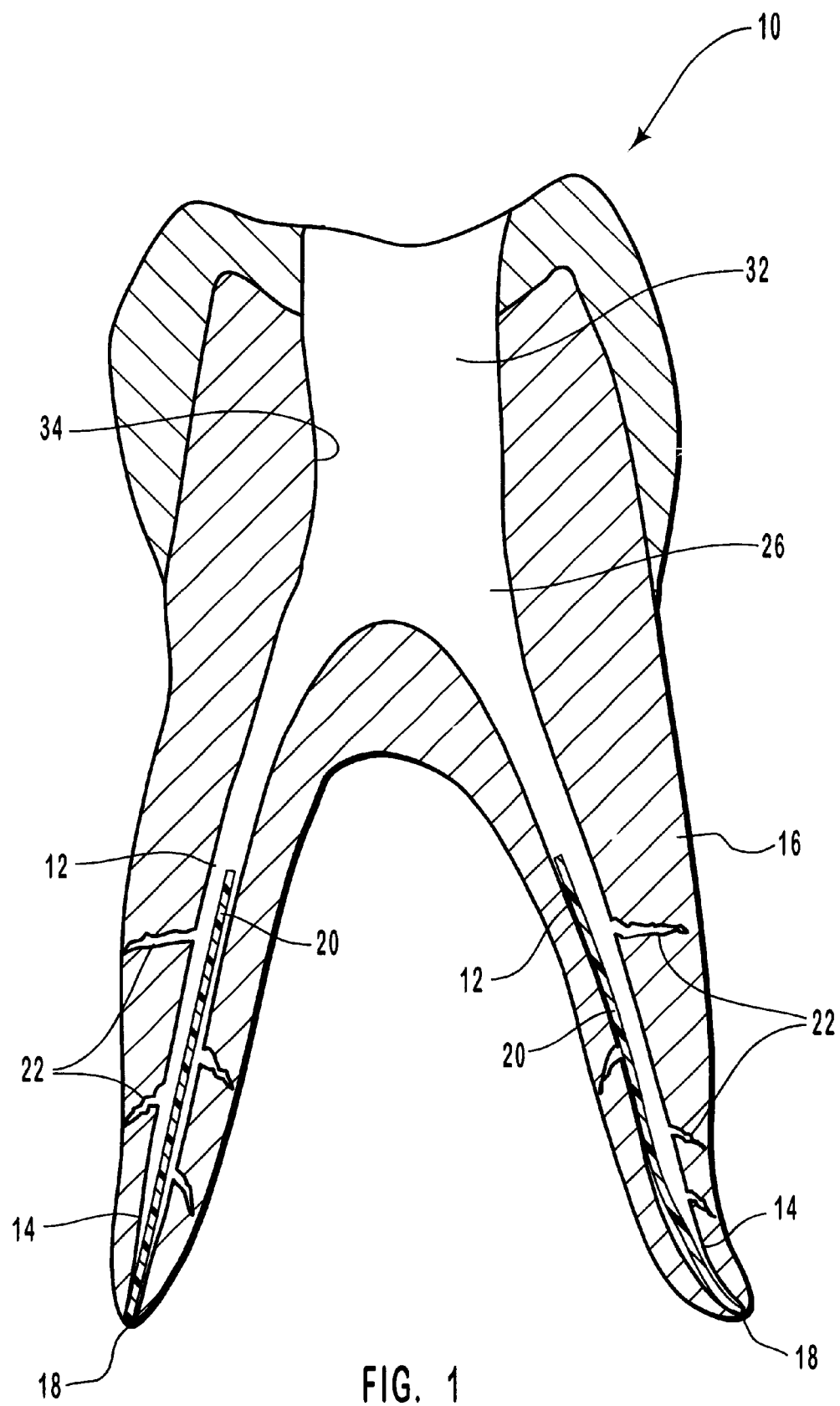
FIG. 1 is a cross sectional view of a tooth showing a root canal with a gutta percha cone inserted into the apex so as to seal the apex and provide a fluid-tight seal.

The present invention is directed to polymerizable resins used fill a root canal during endodontic procedures. The invention also related to improved procedures for placing the inventive sealing or filling resins, as well as conventional resins or pastes, within a root canal. To provide better compatibility with the hydrophilic environment within a tooth, the adhesive sealing or filling resins advantageously include a component that is compatible with hydrophilic and mineralized dental tissues. Increased hydrophilic compatability facilitates wetting of the dental tissue, enables penetration of the sealing material within gaps, spaces and lateral canals associated with the root canal, and promotes penetration into the dentinal tubules and, hence, superior adhesion to the dental tissue surrounding the root canal.

Sealing or filling resins and other flowable sealing or filling materials may optionally be placed within a root canal by means of pressurized hydraulic systems or devices able to deliver viscous fluids through narrow cannulas placed within the root canal. Once placed, the sealing resins or other materials are advantageously forced under pressure into the lateral canals associated with the main root canal branches, thus providing a much better seal of the root canal. This may be accomplished by means of a mini syringe-like plunger or like device that works in conjunction with a customized bore through the crown of the tooth.

The adhesive sealing or filling resins within the scope present invention typically include one or more monomers that promote adhesion, such as methacrylate monomers having an oxyphosphorus constituent, a radio opacifying agent, and one or more types of polymerization initiators. The term "radiopaque" refers to materials that allow the composition to be more easily seen using an X-ray. The composition may also include other additives such as diluent monomers, fillers, antimicrobial agents, plasticizers, solvents and the like.

The compositions and methods are effective in reliably sealing the root canal from the ingress of fluids and bacteria from the crown and/or periodontal tissue. This helps to ensure the mechanical integrity of the treated tooth. Equally or more important, it protects surrounding bone from being infected by bacteria that may have otherwise infected the treated tooth. In a preferred embodiment, the sealing or filling resins may be dual curable, that is, curable both chemically and by irradiation with light energy. This gives the dentist greater control over the time it takes to provide sufficient curing of the sealing or filling resin to permit placement of a final filling material or prosthetic covering.

II. Endodontic Sealing or Filling Compositions

A wide variety of polymerizable monomers, radiopaque materials, initiators, and other components may be used within the inventive endodontic sealing or filling compositions within the scope of the invention, including those disclosed in U.S. Pat. No. 6,071,528 to Jensen and presently assigned to Ultradent Products, Inc. located in South Jordan, Utah. For purposes of disclosure, the foregoing patent is incorporated herein by specific reference.

The compositions within the scope of the invention can be chemically curable, photo curable, or dual cure. In the case of chemical and dual cure sealing or filling compositions it will typically be necessary to provide a two-part (or multi-part) composition that is mixed by the dentist just prior to use. One part will include all the constituents of the resin sealing or filling together with one half of the chemical cure system (e.g., a peroxide compound), while another part will include all the constituents of the resin sealing with the other half of the chemical cure system (e.g., an amino compound). In the case of a photocured sealing or filling composition, the polymerizable resin will advantageously be stable in the presence of the photoinitiator absent the application of radiant energy.

In the case of chemically cured systems, the final endodontic sealing or filling composition, upon mixing the multiple parts together, will preferably cure within a time period of about 15 minutes to about 2 hours, more preferably in a range of about 30 minutes to about one hour.

On the other hand, in the case of a photo cured system, including dual cure systems, irradiating the sealing or filling composition with radiant energy, such as from a ultraviolet curing lamp, can effect much more rapid curing than chemical cure alone. The upper 1–3 mm of sealing or filling material within the root canal can typically be photo cured in a period of time of from about 10 seconds to about one minute.

A. Adhesion and Diluent Monomers.

The polymerizable sealing or filling compositions according to the invention include at least one adhesion monomer that is at least partially hydrophilic and/or includes constituents which make an otherwise hydrophobic resin more adhesive to dental tissue. The adhesion monomers within the scope of the invention may include any monomer that yields a composition that is capable of wetting and penetrating into the dentinal tubules. General examples include a wide range of acrylates, methacrylates, alkylhydroxy methacrylates, alkylamino methacrylates, and derivatives thereof. More specific examples of adhesion monomers include glycidyl dimethacrylate, 2-hydroxy ethyl methacrylate, 3-hydroxy propyl methacrylate, 4-hydroxy butyl methacrylate, triethylene glycol dimethacrylate, and polyethylene glycol dimethacrylate.

In a most preferred embodiment, the adhesion monomer may include an oxyphosphorus alkyl methacrylate. The currently preferred oxyphosphorus alkyl methacrylate comprises bis glycerol dimethacrylate phosphate. Examples of other oxyphosphorus alkyl methacrylates within the scope of the invention include bis 2-hydroxy ethyl methacrylate phosphate, phosphate ester of p-hydroxyphenyl methacrylamide, phosphate ester of 3-hydroxy propyl methacrylate, and phosphate ester of 4-hydroxy butyl methacrylate. Notwithstanding the foregoing examples, the oxyphosphorus alkyl methacrylate can be any alkyl methacrylate having an oxyphosphorus group or phosphorus acid group selected from the group consisting of:

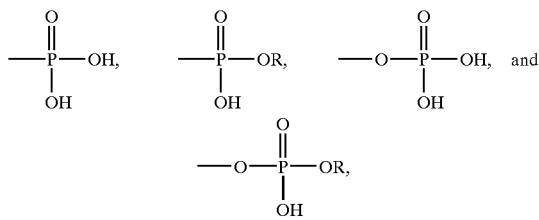

wherein R is an alkyl or aryl.

The oxyphosphorus group not only tends to increase the adhesiveness of the resin compared to analogous compounds lacking this added constituent, but it also increases the water solubility, or relative hydrophilicity, of the resulting resin. In an informal comparison of the relative water solubilities of glycidyl dimethacrylate and bis glycerol dimethacrylate phosphate, the latter was found to be considerably more water soluble compared to the former. On this basis, it was presumed that the addition of the oxyphosphorus group increased the hydrophilicity of the resulting compound compared to the original compound.

In addition to the adhesion monomer, the compositions according to the invention may include one or more additional (or diluent) monomers to achieve the desired properties of initial flowability, curability, and final cured strength and hardness. In the case where the adhesion monomer includes an oxyphosphorus alkyl methacrylate, the diluent monomer may include any of the non oxyphosphorus monomers listed above. In addition, monomers that are hydrophobic yet suitable as diluent monomers include urethane dimethacrylate, p-hydroxyphenyl methacrylamide, butane diol dimethacrylate, and bisphenol-A-diglycidyl dimethacrylate ("Bis-GMA").

The adhesion monomers are preferably included in a concentration ranging from about 0.01% to about 90% by weight of the composition, more preferably from about 0.5% to about 30% by weight, and most preferably from about 1% to about 10% by weight of the composition.

The diluent monomers may be included in amounts of up to about 95% by weight of the composition, preferably in a range from about 5% to about 80%, and more preferably in a range from about 10% to about 70% by weight of the composition.

B. Initiators.

Initiators are provided in the composition to induce polymerization of the monomer. The initiators or curing agents may include radiant energy polymerization initiators with or without an appropriate organic amine additive or a chemical initiator with an appropriate organic amine additive.

1. Photoinitiators.

Examples of photoinitiators within the scope of the invention include camphor quinone, benzoin methyl ether, 2-hydroxy-2-methyl-1-phenyl-1-propanone, diphenyl2,4,6-trimethylbenzoyl phosphine oxide, benzoin ethyl ether, benzophenone, 9,10-anthraquinone, and derivatives thereof.

Photoinitiators are preferably included in an amount in a range from about 0.05% to about 5% by weight of the composition, more preferably in a range from about 0.1% to about 2% by weight, and most preferably in a range from about 0.2% to about 1% by weight of the composition.

2. Chemical Initiators.

Examples of chemical initiators include a wide range of peroxides, other per components, and other free radical generators. A two-part chemical curing system typically includes a peroxide constituent in one part and an amino compound in another. Exemplary peroxides include benzoyl peroxide, 2-butanone peroxide, lauroyl peroxide and tert-butyl peroxide. Examples of amino compounds include dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, and derivatives thereof.

In a preferred embodiment, the chemical initiator will be selected and included in an amount so as to provide sufficient time to allow the dentist or dental practitioner to have sufficient time to place the resinous sealing or filling material into the root canal and cause it to flow into the lateral canals. In other words, once mixed, the curing time will be sufficiently long so as to allow the dentist to carry out a desired sealing and/or filling procedure. On the other hand, unlike conventional sealers, which often cure very slowly, sometimes over a period of one or more days, the sealing and filling materials of the invention are typically formulated so that they will cure more rapidly, typically in 2 hours or less in order to inhibit or avoid leaching of the polymerizable monomer into the surrounding dental tissue.

In most cases, it will be advantageous to include a chemical curing agent in order for the polymerizable resin to cure within a time period of about 20 minutes to about 2 hours, more preferably from about 30 minutes to about one hour. Such time periods generally provide sufficient time to determine whether or not the sealing material has been properly placed. If not, the uncured resin can be removed and replaced with new resin in a follow-up procedure.

Chemical initiators are preferably included in an amount in a range from about 0.01% to about 5% by weight of the composition, more preferably in a range from about 0.05% to about 2% by weight, and most preferably in a range from about 0.1% to about 1% by weight of the composition.

C. Radiopague Fillers.

Radiopaque fillers are advantageously included in order to provide the ability of the dentist to X-ray and determine how well the endodontic resin has penetrated into and filled the root canal, including the lateral canals. Examples of fillers that can provide increased radio opacity include bismuth salts such as bismuth chloride, silver and silver salts such as silver chloride, barium salts such as barium sulfate or barium chloride, tungsten salts, titanium dioxide, and strontium salts such as strontium sulfate and strontium chloride. These and other fillers such as silicon dioxide and calcium phosphate tribasic may also be used to minimize polymerization shrinkage and the total heat potential of polymerization.

It is within the scope of the invention to include fillers in an amount of up to about 85% by weight of the composition, more preferably in a range from about 2% to about 70% by weight, and most preferably in a range from about 5% to about 50% by weight of the composition.

D. Antimicrobial Agents.

The sealing or filling compositions may optionally include one or more antimicrobial agents to assist in cleansing and sterilizing the root canal and to prevent later infection. Examples of suitable antibacterial agents include organohalogens, antibiotics, alkali metal hydroxides, alkaline earth metal oxides, and alkaline earth metal hydroxides.

Examples of antibacterial organohalogens include 1,1'-hexamethylene bis(5(p-chlorophenyl)biguanide), cetyl pyridinium chloride, benzalkonium chloride, and cetyl pyridinium bromide.

Examples of suitable antibiotics include: 4'-sulfamoylsulfanilanilide, 3-amino-6-(2- (5-nitro-2-furyl)vinyl)pyridazine, trans-pseudomonic acid, xanthomycin, alpha-amino-p- toluene sulfonamide, alpha-azido benzyl penicillin, penicillin O, penicillin N, monopropionyl erthromycin, and erythromycin 9(O-((2-methoxy ethoxy) methyl) oxime.

Examples of suitable alkali metal hydroxides include sodium hydroxide and lithium hydroxide.

Examples of suitable alkaline earth metal oxides include calcium oxide, magnesium oxide, barium oxide, and strontium oxide.

Examples of suitable alkaline earth metal hydroxides include calcium hydroxide, magnesium hydroxide, barium hydroxide, and strontium hydroxide.

A more preferred antimicrobial agent is calcium hydroxide since calcium hydroxide not only kills microorganisms but is chemically compatible with dental tissue. The antimicrobial agent may be included in an amount in a range from about 0.001% to about 30% by weight of the composition, preferably in a range from about 0.005% to about 10% by weight, and most preferably in a range from about 0.01% to about 5% by weight of the composition.

E. Other Additives.

It is certainly within the scope of the invention to include other additives or adjuvents as desired in order to impart a desired property, such as less or non radiopaque fillers, solvents, dyes or plasticizers. For example, silica may be included in order to impart hardness in the case where a sealing filler material is desired. Keeping the silica content low, however, improves the ability to later drill out a portion of the cured material if desired, such as to place a post during a crown restoration.

III. Methods for Sealing Root Canal with Endocontic Resins

An exemplary method for placing and then curing an endodontic sealing or filling resin within a root canal is illustrated in FIGS. 1–5. FIG. 1 depicts a tooth 10 that has been subjected to a root canal procedure. The tooth 10 includes a pair of root canals 12, each of which terminates at an apex 14 that extends through the bottom of the root 16. An opening 18 through the crown of the tooth provides access to the root canals 12, thereby permitting endodontic tools (not shown) to be inserted into the root canals 12. A gutta percha cone 20 has been inserted into each opening 18 in order to seal the apex 14 of each root canal 12 to prevent flow of sealing material into the surrounding bone tissue.

In order to ensure that the gutta percha cone 20 forms a reliable seal within the apex 14, a procedure involving "tug back" is preferably performed. In this procedure, the gutta percha cone is inserted and removed, sometimes more than one time, to determine how much force is needed to remove the gutta percha cone. If it can be removed with little or no force, there is insufficient tug back, and the gutta percha point is trimmed to yield a larger diameter tip and reinserted into the apex. This process is repeated until there is sufficient tug back, or resistance, felt by the dentist or dental practitioner. One of ordinary skill in the art of endodontics will know when there is sufficient tug back to confirm an adequate seal of the apex 14 by the gutta percha cone 20. Sufficient tug back indicates that the fit between the gutta percha cone and the apex is sufficiently tight to adequately seal the apex and prevent flow of sealing or filling material therethrough into the surrounding bone tissue.

In addition to the root canals 12, lateral canals 22 extend from the root canals 12 and provide communication between the root canals 12 and the surrounding periodontal tissue of the lower portion of the tooth. The lateral canals 22 are particularly difficult to seal using conventional compositions and methods. The inventive compositions and methods, however, facilitate penetration of resinous sealing or filling material into the lateral canals 22.

Figure 2:
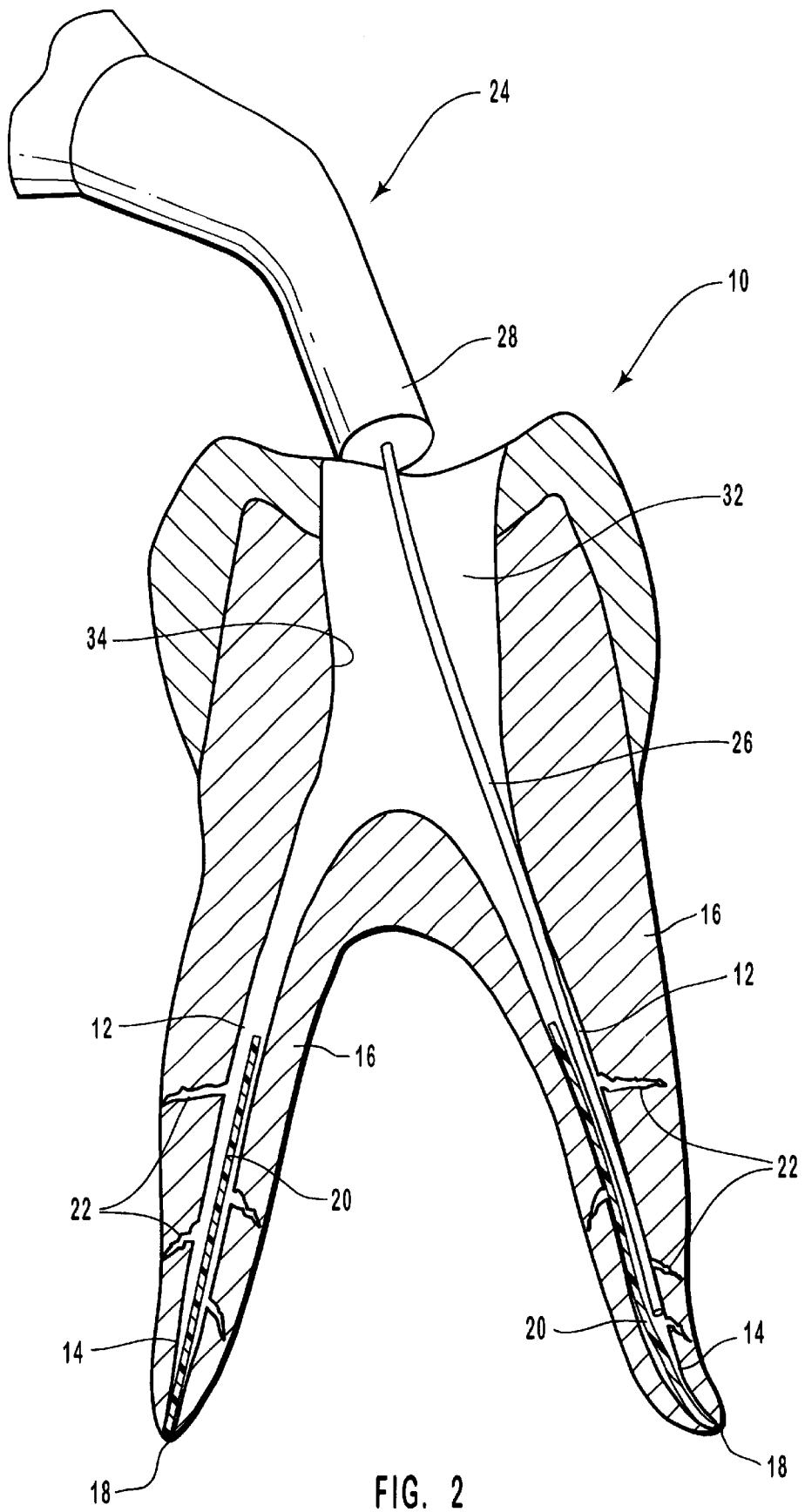
FIG. 2 is a cross sectional view of the tooth of FIG. 1 in which a small diameter cannula device has been inserted within the root canal for the purpose of filling the root canal with an endodontic sealing or filling resin.

In a preferred method for placing a resinous sealing or filling material within a root canal, FIG. 2 depicts a syringe tip 24 having a narrow diameter cannula 26 attached to an enlarged portion 28 of the syringe tip 24 used to insert sealing or filling material into the canal 12. Due to the narrow opening of the cannula 26, and because typical sealing or filling materials often sufficiently viscous that they may not readily pass through the cannula 26, it will generally be advantageous for the syringe tip 24 to be attached to a high pressure hydraulic injection system (not shown). An example of high pressure hydraulic syringes or systems are set forth in the aforementioned copending U.S. application Ser. No. 09/467,419, filed Dec. 20, 1999. Examples of narrow cannulas sized for entry into a root canal are set forth in U.S. Pat. No. 6,079,979, which is assigned to Ultradent Products, Inc. For purposes of disclosing hydraulic pressurizing systems and cannulas sized to fit within a root canal, the foregoing patent application and patent are incorporated herein by specific reference.

The tip of the cannula 26 is initially placed within the root canal 12 near the apex 14, and sealing or filling material (not shown) is expressed therefrom into the root canal 12. As the resinous material begins and continues to fill up the root canal 12, the cannula 26 is slowly raised or withdrawn from the root canal 12. This manner of filling the root canal 12 with resinous material minimizes or eliminates the formation of air pockets or bubbles as the resin is progressively placed within the root canal 12. This procedure greatly improves the ability of the resin to initially purge most or all of the air from within the root canal 12 compared to simply dipping a gutta percha point in the resin and stuffing the point into a root canal, as is conventionally done.

Figure 3:
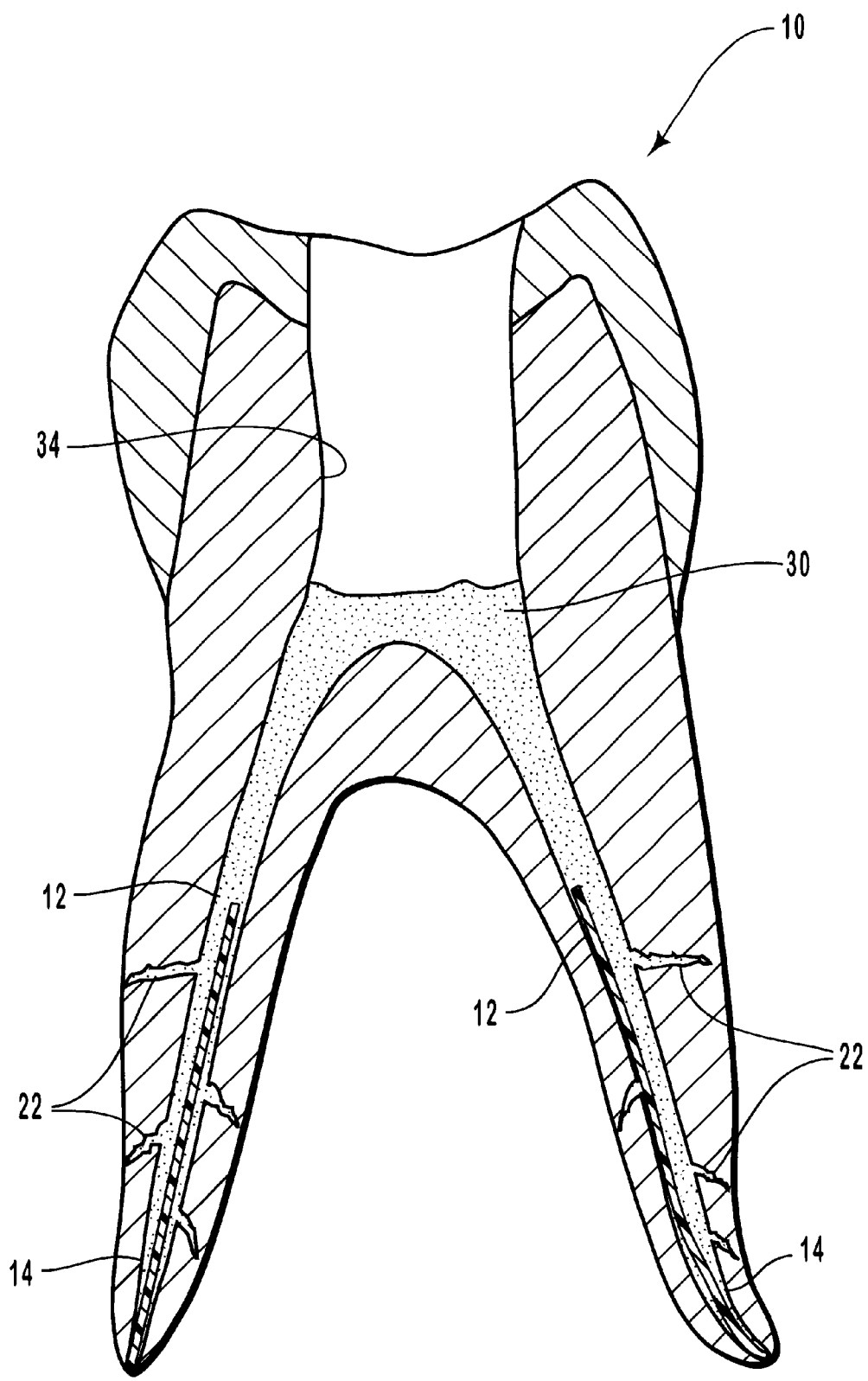
FIG. 3 is a cross sectional view of the tooth of FIGS. 1 and 2 after the root canal has been filled with an endodontic sealing or filling resin.
Figure 4A:
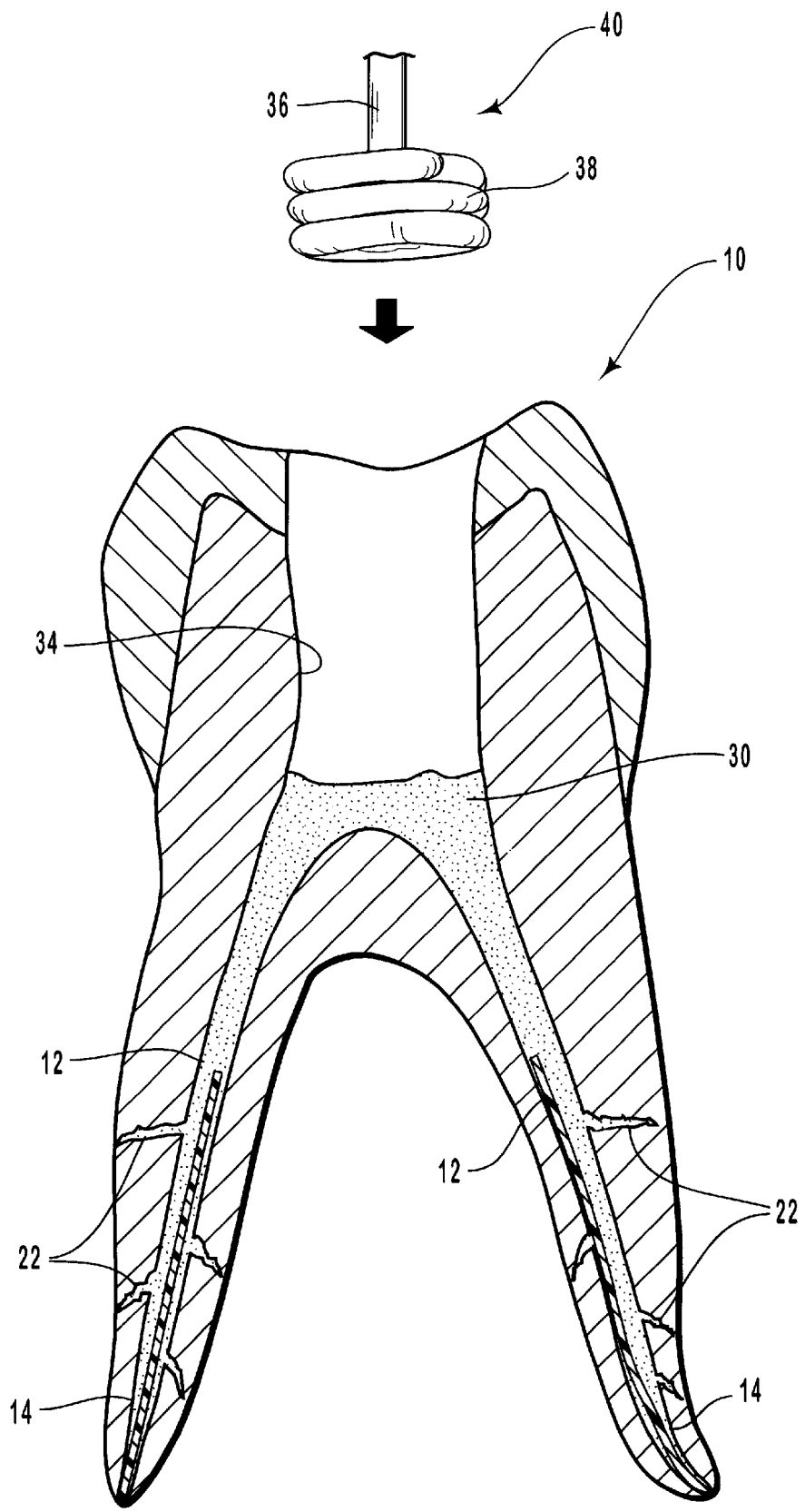
FIG. 4A is a cross sectional view of the tooth of FIG. 3 in which a portion of a gutta percha cone has been wrapped around the end of a wire preparatory to heating and melting the gutta percha to form a syringe-like plunger to be inserted into the tooth.
Figure 4B:
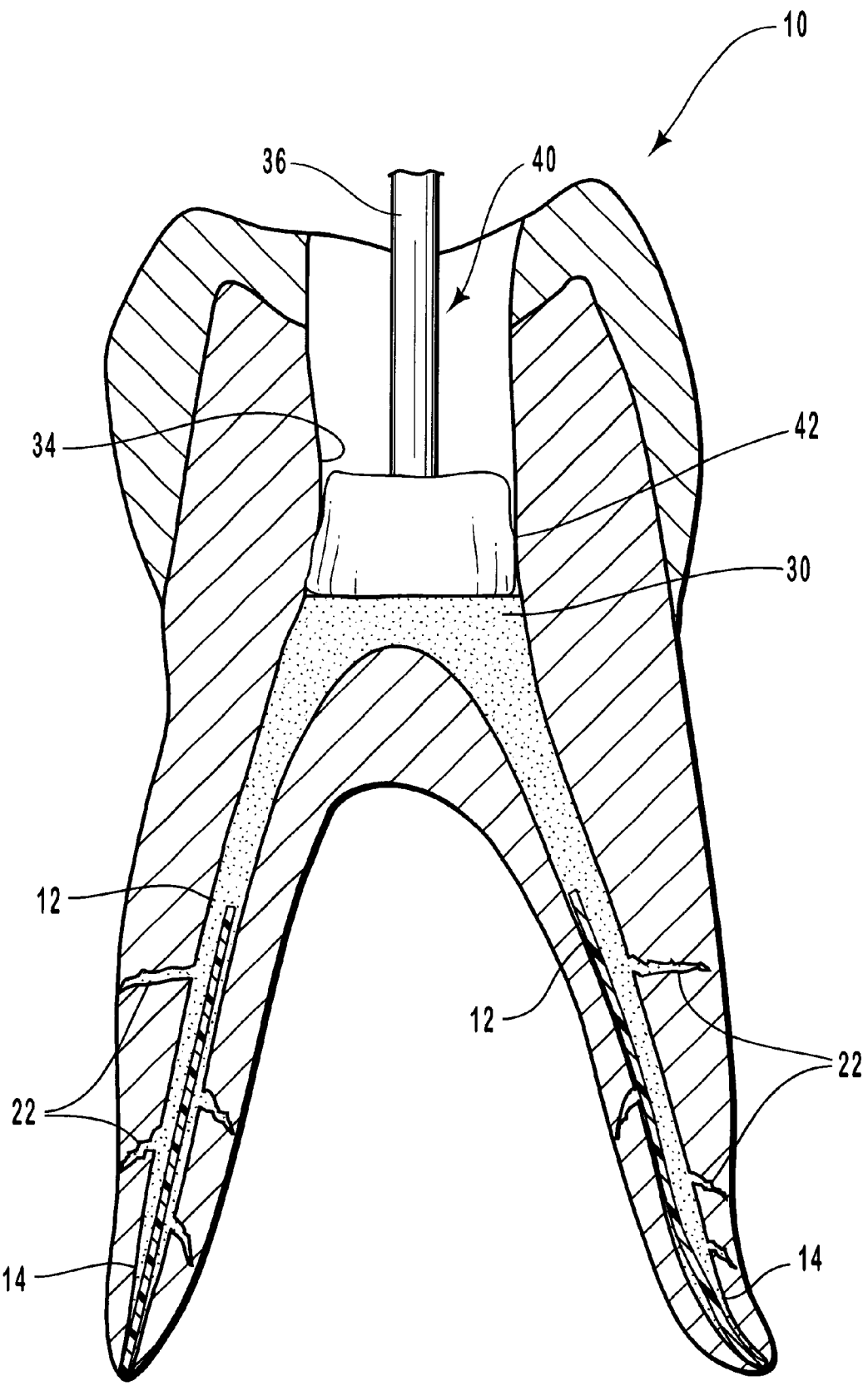
FIG. 4B is a cross section view of the tooth of FIG. 4A in which the gutta percha has been melted and conformed to the diameter of the opening in the tooth so as to form a plunger-like device used to exert pressure onto the endodontic sealing or filling resin to force the resin into the lateral microfissures in communication with the root canal.

FIG. 3 depicts a tooth 10 into which a resinous sealing or filling material 30 has been successfully placed within the root canals 12, with little or no formation of air pockets. Even so, initial placement of the resin 30 in this manner does not typically result in complete filling of the lateral canals 22. To ensure that the endodontic sealing or filling material 30 has penetrated into and sealed every space, irregularity or lateral canal 22 of the root canal 12, it may be advantageous to apply additional pressure to the resin 30 after it has been initially placed within the root canals 12. In one embodiment, additional pressure may be applied by inserting a plunger-like device into a hole 32 through the crown 33 of the tooth 10 that is initially made to provide access to the root canals 12 during the root canal procedure. FIGS. 4A and 4B illustrate this optional procedure.

In order for the plunger-like device to work in applying sufficient pressure so that the filling or sealing resin 30 is forced into the lateral canals 22, it will be advantageous to provide a resilient plug-like material that is able to conform to and seal against the inner wall 34 of the tooth 10 defining the hole 32. The resilient plug-like material will preferably have a diameter that is complementary to the diameter of the hole 32. Although the plunger-like device may include any resilient plug-like material, in a presently preferred method, the resilient plug-like material is formed from excess gutta percha material that is trimmed off of the gutta percha cone 20.

As more clearly depicted in FIG. 4A, a length of excess gutta percha is wrapped around a wire 36 to form a gutta percha wrap or bundle 38 to form a plunger 40. Heat is then applied to the wire 36 in order to cause the gutta percha wrap or bundle 38 to melt slightly so that it coalesces together to form the resilient plug-like material. While the gutta percha bundle 38 bundle is in a plastic state, the plunger 40 is placed into the hole 32 of the tooth 10 in order to allow the gutta percha bundle to flow or otherwise conform to the size and shape of the hole 32.

As shown in FIG. 4B, once the gutta percha bundle 38 has coalesced together and conformed to the shape of the hole 32, it yields a plunger 40 having a gutta percha plug 42 on the end thereof. The gutta percha plug 42 is allowed to cool and thereby adhere to the wire 36. Thereafter, the wire 36 and gutta percha plug 42 yield a plunger 40 that can be used to exert pressure on the resinous sealing or filling material 30 in order to force it to flow into the cracks, crevices and lateral canals 22 that may extend from the root canal 12. In addition, pressure applied by the plunger 40 may also assist the resin 30 to flow into the dentinal tubules in order to promote better adhesion between the resin 30 and the dental tissue surrounding the root canal 12.

As depicted in FIG. 4B, force applied to the plunger 40 in a direction from the crown of the tooth 10 towards the apex 14 of the root canals 12. Force maybe applied to the plunger 40 manually or by means of pliers or other gripping tools. Pressure is maintained on the resinous sealing or filling material 30 because the elastomeric plug 42 seals against the inner wall 34 defining the hole 32 through the crown 33 of the tooth 10. Because of this, the resinous material 30 is not able to squeeze out in appreciable amounts between the tooth wall 34 and the resilient plug 42. Instead, the pressure exerted onto the resinous material 30 forces it into the aforementioned spaces, crevices or canals. In this manner, the resinous sealing material 30 is able to form a substantially hermetic seal of the root canals 12.

Although FIGS. 4A and 4B depict a preferred method for forming a suitable plunger 40 for use in applying pressure to the resinous sealing or filling material 30, it should be understood that plunger-like devices or other pressurizing means would be within the scope of the invention. In view of the present disclosure, one of ordinary skill could design other pressuring means that would work to apply pressure to the resin 30. For example, in place of gutta percha, the plunger 42 may comprise any resilient or elastomeric material that can seal against the inner wall of the hole 32 through the crown. Examples include other natural rubbers, silicone rubbers and other synthetic rubbers or elastomers.

Providing a more complete seal of the root canal 12 greatly increases the ability of the sealed root canals 12 to resist the ingress of fluids therein. Such fluids may enter the root canals 12, for example, through fissures in the crown and/or periodontal tissue. Such fluids, if allowed to enter the root canals 12, may carry microbes capable of attacking and decaying the dental tissue surrounding the root canals 12, thus compromising the mechanical integrity of the dead tooth 10 and, more importantly, potentially infecting surrounding teeth. In improving the ability of the resinous material 30 to more effectively seal the root canals 12, including the lateral canals 22 and other crevices that are typically hard to fill, the inventive compositions and methods provide a tremendous advantage over conventional compositions and methods in yielding a tooth that is more resistant to microbial attack.

As set forth above, the resinous sealing or filling materials may be chemically cured, photo cured or dual cured. In a preferred embodiment, the compositions will be dual cured. That is, they will preferably be cured both by means of a chemical curing agent and by the application of radiant energy. Because photo curing is only capable of curing the top layers of the resinous sealing or filling material 30, but is incapable of sealing all the way down to the apex 14 of the root canal 12, photo curing alone is typically insufficient to provide an adequately cured resinous material 30 throughout the entire length of the root canal 12. For this reason, it will typically be necessary to provide chemical curing of the resinous material 30 in order to ensure that resinous material cures completely throughout the entire root canal 12 and associate lateral canals 22, crevices and spaces.

Nevertheless, because chemically cured sealing or filling materials preferably cure slowly over time (e.g., between 20 minutes and 2 hours) so as to provide the dentist with adequate time to mix and then place the sealing or filling material, it may be desirable to speed up the curing process once proper placement of the resinous sealing material has been verified. Once a dentist or other dental practitioner is sufficiently confident that the resinous material has been adequately placed, it may be desirable to speed up the curing process, at least on the surface or upper portion 44 of the resinous material 30, in order to provide a hardened surface 46 to which a composite material (not shown) can be bonded.

Figure 5:
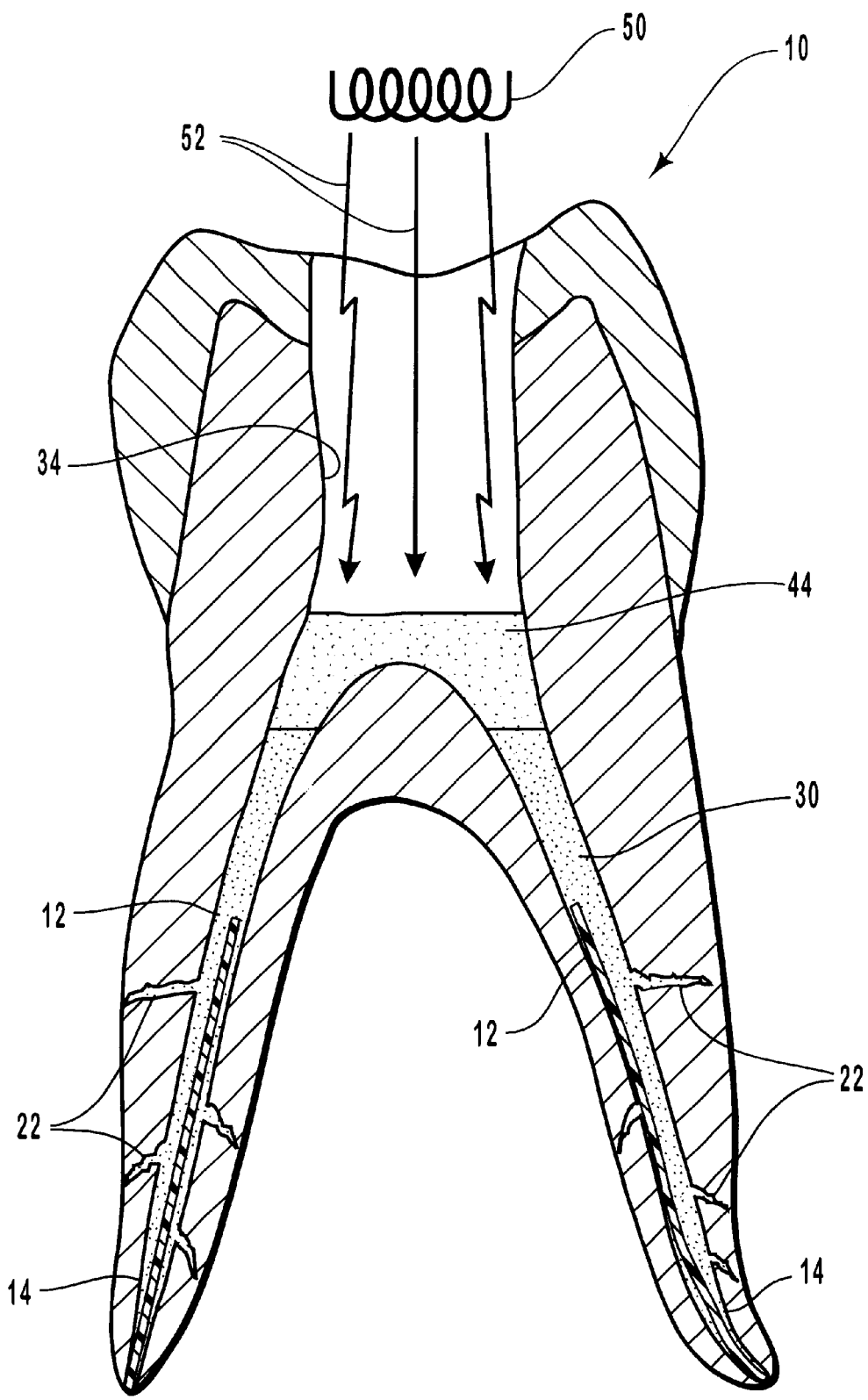
FIG. 5 is a cross section view of a tooth in which the endodontic sealing or filling resin within the root canal is being partially cured using a curing lamp preparatory to placing a final filling material and/or crown to seal the root canal.

As depicted in FIG. 5, a curing lamp 50 that emits radiant energy 52, such as ultraviolet radiation, can be used to cure the top or upper portion 44 of a dual cure sealing or filling material. The photo cured portion 44 will typically only extend partially down the root canal 12 while the remaining portion of the resinous material 30 will extend all the way to the apex 14 of the root canal. The hardened upper portion 44 of the resinous material provides a hardened surface to which a composite filling material (not shown) can immediately be chemically bonded or adhered. This allows the dentist to rapidly complete the endodontic process and eliminates the need for the patient to either sit in the dental chair while the resinous material chemically cures or make a appointment for a follow up visit to receive the final filling material.

It should be understood that the compositions and procedures according to the present invention may be used with or without gutta percha points. One advantage of using gutta percha points is that they can be used to seal the apex 14 with each root canal 12 prior to placing the resinous sealing material therein. This helps to prevent incursion of the sealing or filling material into the surround bone tissue. Another advantage of a gutta percha point is that it provides a path through which a hole can be drilled through the sealed root canal without compromising the surrounding cured sealing or filling material. Such holes are referred to as "channel holes" or "post channel holes". Channel holes may be drilled, for example, in order to place reinforcing posts (not shown) down the root canal in the case of a relatively weak tooth. Posts are also used when attaching a prosthetic crown to a tooth.

On the other hand, the resinous sealing or filling materials according to the present invention will typically be softer than typical composite materials and may be easily drilled in many cases. Because of this, it may be unnecessary to utilize gutta percha points to facilitate the formation of channel holes through the root canal if needed.

Another advantage of the compositions and methods according to the present invention is that they provide a bonding surface to which a composite material, such as materials that include Bis-GMA, can form a chemical or adhesive bond. Prior art antiseptic pastes, such as zinc oxide/eugenol or calcium hydroxide mixed with iodoform, do not provide a bonding surface to which composites can bond. Such materials are generally inert and relatively soft, thus providing neither chemical nor mechanical bonding possibilities. Moreover, to the extent that such materials become interposed between the composite material and the tooth, they may inhibit bonding between the composite material and the tooth. In the case of amalgam, providing a hardened sealing or filling material, at least on the surface of the sealed root canal, will facilitate placement of the amalgam. Because of the soft nature of the prior antiseptic pastes, it was always necessary to utilize a post in order to provide a mechanical attachment surface to which a composite or amalgam filling material could attach. The photocurable sealing or filling materials according to the invention reduce or eliminate the need for such posts.

The resinous sealing or filling materials according to the present invention are also safer compared to prior art sealers, such as 26H or 26 Plus sold by Dentsply, which are known to leach formaldehyde into the surrounding dental tissue.

IV. Examples of the Preferred Embodiments

Several examples of the present invention are presented as merely illustrative of some embodiments of the present invention. These examples are not to be construed as limiting the spirit and scope of the invention. Examples written in past tense refer to actual compositions that have been made, while those in present tense are hypothetical in nature, though based on mix designs that have already been made.

EXAMPLE 1

A dual cure dental composition suitable as an endodontic sealing or filling material was prepared in two parts, with each part having the following components in the stated amounts:

| Part 1 | |
|---|---|
| Triethylene Glycol Dimethacrylate | 16.8% |
| Benzoyl Peroxide | 0.2% |
| Diurethane Dimethacrylate | 30.0% |
| Bis glycerol dimethacrylate phosphate | 5.0% |
| Bismuth Chloride Oxide | 40.0% |
| Calcium Lactate Pentahydrate | 6.0% |
| Silicon Dioxide | 2.0% |
| Total Part 1: | 100% |

| Part 2 | |
|---|---|
| Triethylene Glycol Dimethacrylate | 16.8% |
| p-Tolyimino Diethanol | 0.2% |
| Phenyl bis(2,4,6-trimethyl benzoyl) Phosphine Oxide | 0.5% |
| Diurethane Dimethacrylate | 30.0% |
| Bis glycerol dimethacrylate phosphate | 5.0% |
| Bismuth Chloride Oxide | 40.0% |
| Calcium Lactate Pentahydrate | 5.5% |
| Silicon Dioxide | 2.0% |
| Total Part 2: | 100% |

The final composition was made by mixing equal amounts of Parts 1 and 2. Once mixed, the mixed composition was able to cure in less than 2 hours, thus preventing or inhibiting leaching of monomers and other materials from the root canal into the surrounding dental tissues. The mixed composition was also capable of accelerated curing as a result of irradiating the composition with radiant energy, such as by means of a dental curing lamp.

EXAMPLE 2

An adhesive antimicrobial dental composition was formed having the following components and concentrations:

| Component | Percent by Weight of the Mixture |
|---|---|
| calcium hydroxide | 10.0% |
| bis-glycerol methacrylate phosphate | 5.0% |
| urethane dimethacrylate | 57.0% |
| triethylene glycol dimethacrylate | 6.0% |
| titanium dioxide | 1.0% |
| calcium phosphate tribasic | 10.0% |
| dimethyl amino ethyl methacrylate | 0.5% |
| camphorquinone | 0.2% |
| barium sulfate | 10.3% |

EXAMPLE 3

In this example, an adhesive antimicrobial dental composition is formed having the following composition:

| Component | Percent by Weight of the Mixture |
|---|---|
| bis 2-hydroxy ethyl methacrylate | 10.0% |
| barium hydroxide | 25.0% |
| calcium phosphate tribasic | 5.0% |
| benzoin ethyl ether | 0.4% |
| N-methylethanol amine | 0.5% |
| glycerol dimethacrylate | 59.1% |

EXAMPLE 4

In this example, an adhesive antimicrobial dental composition is formed having the following composition:

| Component | Percent by Weight of the Mixture |
|---|---|
| strontium oxide | 30.0% |
| camphorquinone | 0.5% |
| diethyl amino ethyl methacrylate | 0.5% |
| bis glyceryl methacrylate phosphate | 69.0% |

EXAMPLE 5

In this example, an adhesive antimicrobial dental composition is formed having the following composition:

| Component | Percent by Weight of the Mixture |
|---|---|
| cetyl pyridinium chloride | 4.0% |
| strontium chloride | 10.0% |
| 2-hydroxy-2-methyl-1-phenyl-1-propanone | 0.5% |
| diphenyl 2,4,6-trimethylbenzoyl phosphine oxide | 0.5% |
| xanthomycin | 1.0% |
| phosphate ester of 4-hydroxy butyl methacrylate | 29.0% |
| butane diol dimethacrylate | 55.0% |

EXAMPLE 6

In this example, an adhesive antimicrobial dental composition is formed having the following composition:

| Component | Percent by Weight of the Mixture |
|---|---|
| penicillin N | 3.5% |
| silicon dioxide fumed | 16.0% |
| bis-glyceryl methacrylate phosphate | 3.0% |
| benzophenone | 1.0% |
| tri hexyl amine | 1.5% |
| calcium phosphate tribasic | 10.0% |
| bis 2-hydroxy ethyl methacrylate | 4.0% |
| triethylene glycol dimethacrylate | 61.0% |

EXAMPLE 7

In this example, an adhesive antimicrobial dental composition is formed having the following composition:

| Component | Percent by Weight of the Mixture |
|---|---|
| 4'-sulfamoylsulfanilanilide | 1.0% |
| 1, 1'-hexamethylene bis (5(p-chlorophenyl) biguanide) | 1.0% |
| phosphate ester of 3-hydroxy propyl methacrylate | 5.0% |
| urethane dimethacrylate | 92.0% |
| benzoin ethyl ether | 1.0% |
| 2-dimethylaminoethanol | 1.0% |

EXAMPLE 8

In this example, an adhesive antimicrobial dental composition is formed having the following composition:

| Component | Percent by Weight of the Mixture |
| --- | --- |
| magnesium oxide | 15.0% |
| barium chloride | 40.0% |
| 9, 10-anthraquinone | 0.9% |
| triethylamine | 0.3% |
| bis glyceryl methacrylate phosphate | 43.8% |

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for treating a tooth following an endodontic procedure comprising:

providing a tooth that includes an access hole drilled into and extending through the crown of the tooth, said access hole providing access to at least one root canal of the tooth that has been cleaned by an endodontic procedure;

mixing together initially separate parts of a multipart endodontic composition to form a mixed composition which is initially flowable and suitable for placement into a root canal during a root canal procedure and which hardens over time, the mixed composition initially including:

a polymerizable resin portion including an adhesive resin that is at least one of an alkyl acrylate or alkyl methacrylate and capable of bonding to dental tissue found within a root canal;

at least one chemical initiator which causes at least a portion of the polymerizable resin portion to polymerize over a period of time; and at least one polymerization photoinitiator which, upon irradiating at least a portion of the mixed composition with radiant energy, causes accelerated polymerization and hardening of at least a portion of the polymerizable resin portion;

introducing the mixed composition into the at least one root canal of the tooth;

irradiating with radiant energy an exposed portion of the mixed composition within the root canal in order to polymerize and harden at least the exposed portion of the mixed composition; and filling the access hole with a filling material.

2. A method for treating a tooth as defined in claim 1, wherein the adhesive resin has an initial concentration in a range from about 0.01% to about 90% by weight of the mixed composition.

3. A method for treating a tooth defined in claim 1, wherein the adhesive resin has an initial concentration in a range from about 0.5% to about 30% by weight of the mixed composition.

4. A method for treating a tooth defined in claim 1, wherein the adhesive resin has an initial concentration in a range from about 1% to about 10% by weight of the mixed composition.

5. A method for treating a tooth defined in claim 1, wherein the polymerizable resin portion further includes at least one additional polymerizable resin comprising at least one of an alkyl acrylate, an alkyl methacrylate, an alkyl hydroxy methacrylate, an alkyl amino methacrylate, or bisphenol-A-diglycidyl dimethacrylate.

6. A method for treating a tooth as defined in claim 5, wherein the at least one additional polymerizable resin has an initial concentration of up to about 95% by weight of the mixed composition.

7. A method for treating a tooth as defined in claim 5, wherein the at least one additional polymerizable resin has an initial concentration in a range from about 5% to about 80% by weight of the mixed composition.

8. A method for treating a tooth as defined in claim 5, wherein the at least one additional polymerizable resin has an initial concentration in a range from about 10% to about 70% by weight of the mixed composition.

9. A method for treating a tooth as defined in claim 1, wherein the at least one chemical initiator includes a plurality of initially separate and unmixed components, each component being contained in a different one of the initially separate parts of the multipart endodontic composition.

10. A method for treating a tooth as defined in claim 9, wherein the at least one chemical initiator includes a peroxide-based component contained in one of the initially separate parts and an amino component contained in a different one of the initially separate parts.

11. A method for treating a tooth as defined in claim 10, wherein the peroxide-based component includes at least one of benzoyl peroxide, 2-butanone peroxide, lauroyl peroxide, or tert-butyl peroxide.

12. A method for treating a tooth as defined in claim 10, wherein the amino component includes at least one of dimethylamino ethyl methacrylate, triethyl amine, 2-dimethylamino ethanol, diethylamino ethyl methacrylate, trihexyl amine, N,N-dimethyl-p-toluidine, N-methylethanolamine, or 2,2'(p-tolyimino) diethanol.

13. A method for treating a tooth as defined in claim 1, wherein the at least one polymerization photoinitiator includes at least one of camphor quinone, benzoin methyl ether, 2-hydroxy-2-methyl-1-phenyl-1-propanone, diphenyl 2,4,6-trimethylbenzoyl phosphine oxide, benzoin ethyl ether, benzophenone, or 9,10-anthraquinone.

14. A method for treating a tooth as defined in claim 1, the multipart endodontic composition further including a radiopaque filler contained in at least one of the initially separate parts that is at least one of a bismuth salt, silver, a silver salt, a barium salt, a strontium salt, a tungsten-containing compound, or titanium dioxide.

15. A method for treating a tooth as defined in claim 1, the multipart endodontic composition further including at least one of silica or calcium phosphate tribasic contained in at least one of the initially separate parts.

16. A method for treating a tooth as defined in claim 1, the multipart endodontic composition further including at least one antimicrobial agent contained in at least one of the initially separate parts.

17. A method for treating a tooth as defined in claim 1, wherein the multipart composition includes two initially separate and unmixed parts.

18. A method for treating a tooth as defined in claim 1, wherein the filling material chemically bonds to the exposed portion of the mixed composition.

19. A method for treating a tooth as defined in claim 1, wherein the mixed composition is introduced into the root canal by means of a cannula sized to fit within the root canal and in fluid communication with a high pressure hydraulic system.

20. A method for treating a tooth as defined in claim 1, further including the step of applying additional pressure to the mixed composition after introducing it into the root canal but prior to the irradiating step so as to cause the mixed composition to flow into lateral canals associated with the root canal.

21. A method for treating a tooth as defined in claim 20, wherein the step of applying additional pressure is carried out by means of inserting an elastomeric plug into a said access hole and applying force to said plug in order to exert fluid pressure onto the mixed composition, said elastomeric plug being sized so as to form a substantially fluid-tight seal between said plug and dental tissue surrounding said access hole.

22. A method for treating a tooth as defined in claim 21, wherein said elastomeric plug comprises gutta percha.

23. A method for treating a tooth as defined in claim 1, wherein the chemical initiator is included in an amount so that the polymerizable resin portion within the mixed composition cures in a time period of about 20 minutes to about 2 hours as a result of chemical curing.

24. A method for treating a tooth as defined in claim 1, wherein the polymerization photoinitiator is included in an amount so that the polymerizable resin portion within the mixed composition cures in a time period of about 10 seconds to about 1 minute when the mixed composition is irradiated with radiant energy.

25. A method for treating a tooth as defined in claim 1, wherein the at least one alkyl acrylate or alkyl methacrylate comprising the adhesive resin is substituted with an oxyphosphorus group.

26. A method for treating a tooth as defined in claim 25, wherein the oxyphosphorus group has a formula selected for the group consisting of:

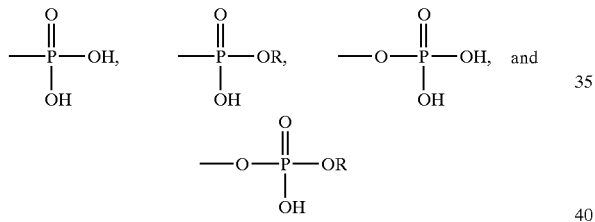

wherein R is an alkyl or aryl.

27. A method for treating a tooth as defined in claim 26, wherein the at least one alkyl acrylate or alkyl methacrylate substituted with an oxyphosphorus group includes at least one of bis 2-hydroxy ethyl methacrylate phosphate, phosphate ester of p-hydroxyphenyl methacrylamide, phosphate ester of 3-hydroxy propyl methacrylate, phosphate ester of 4-hydroxy butyl methacrylate, or bis glycerol methacrylate phosphate.

28. A method for treating a tooth comprising:
preparing an access hole within a tooth so as to expose at least one root canal of the tooth;
performing an endodontic procedure so as to clean the root canal;
mixing together initially separate parts of a multipart endodontic composition to form a mixed composition which is initially flowable and suitable for placement into a root canal and which hardens over time, the mixed composition initially including:
a polymerizable resin portion including an adhesive resin that is at least one of an alkyl acrylate or alkyl methacrylate that promotes bonding to dental tissue found within a root canal;
at least one chemical initiator which causes at least a portion of the polymerizable resin portion to polymerize over a period of time; and
at least one polymerization photoinitiator which, upon irradiating at least a portion of the mixed composition with radiant energy, causes accelerated polymerization and hardening of at least a portion of the polymerizable resin portion;
introducing the mixed composition into the at least one root canal of the tooth;
irradiating with radiant energy an exposed portion of the mixed composition within the root canal in order to polymerize and harden at least the exposed portion of the mixed composition; and
introducing a filling material into the access hole.

29. A method for sealing a root canal of a tooth following an endodontic procedure comprising:
providing a tooth that includes at least one exposed root canal that has been cleaned by an endodontic procedure;
mixing together initially separate parts of a multipart endodontic composition to form a mixed composition which is initially flowable and suitable for placement into a root canal and which hardens over time, the mixed composition initially including:
a polymerizable resin portion including an adhesive resin that is at least one of an alkyl acrylate or alkyl methacrylate and that promotes bonding to dental tissue found within a root canal;
at least one chemical initiator which causes at least a portion of the polymerizable resin portion to polymerize over a period of time; and
at least one polymerization photoinitiator which, upon irradiating at least a portion of the mixed composition with radiant energy, causes accelerated polymerization and hardening of at least a portion of the polymerizable resin portion;
introducing the mixed composition into the at least one root canal of the tooth; and
irradiating with radiant energy an exposed portion of the mixed composition within the root canal in order to polymerize and harden at least the exposed portion of the mixed composition.

* * * * *

UNITED STATES PATENT AND TRADEMARK OFFICE
CERTIFICATE OF CORRECTION

PATENT NO. : 6,500,004 B2
DATED : December 31, 2002
INVENTOR(S) : Steven D. Jensen and Dan E. Fischer It is certified that error appears in the above-identified patent and that said Letters Patent is hereby corrected as shown below:

Column 1,
Line 27, after "order" insert -- to --

Column 6,
Line 44, after "used" insert -- to --
Line 45, change "related" to -- relates --

Column 7,
Line 1, after "scope" insert -- of the --

Column 11,
Line 21, change "tooth ." to -- tooth 10. --

Column 12,
Line 3, delete "33"
Line 23, after "38" delete "bundle"
Line 42, change "maybe" to -- may be --
Line 46, delete "33"

Column 13,
Line 56, change "a" to -- an --
Line 64, change "surround" to -- surrounding --

Column 17,
Line 14, change "illustrated" to -- illustrative --
Line 58, after "tooth" insert -- as --
Line 62, after "tooth" insert -- as --
Line 66, after "tooth" insert -- as --

UNITED STATES PATENT AND TRADEMARK OFFICE
CERTIFICATE OF CORRECTION

PATENT NO. : 6,500,004 B2
DATED : December 31, 2002
INVENTOR(S) : Steven D. Jensen and Dan E. Fischer It is certified that error appears in the above-identified patent and that said Letters Patent is hereby corrected as shown below:

<u>Column 19,</u>
Line 30, change "for" to -- from --

<u>Column 20,</u>
Line 44, change "photoinitiator" to -- photo initiator --

Signed and Sealed this

Eighteenth Day of May, 2004

JON W. DUDAS
*Acting Director of the United States Patent and Trademark Office*